United States Patent [19]

Ford et al.

[11] 4,313,005
[45] Jan. 26, 1982

[54] INHIBITING AMIDINE FORMATION DURING HYDROGENATION OF ORGANO NITRILES

[75] Inventors: Michael E. Ford, Trexlertown; Randall J. Daughenbaugh, Barto, both of Pa.

[73] Assignee: Air Products and Chemicals, Inc., Allentown, Pa.

[21] Appl. No.: 137,052

[22] Filed: Apr. 3, 1980

[51] Int. Cl.$^3$ .................. C07C 85/12; C07C 85/26
[52] U.S. Cl. .................. 564/493; 260/465.5 R; 560/101; 560/102; 560/103; 560/110; 560/116; 560/117; 560/118; 560/129; 564/84; 564/94; 564/98; 564/180; 564/182; 564/183; 564/188; 564/189; 564/190; 564/192; 564/340; 564/341; 564/343; 564/346; 564/347; 564/348; 564/352; 564/356; 564/358; 564/366; 564/367; 564/372; 564/375; 564/490; 564/491
[58] Field of Search .................. 260/583 K; 564/490, 564/493, 356, 358, 343, 375

[56] References Cited

U.S. PATENT DOCUMENTS

| | | | |
|---|---|---|---|
| 2,784,232 | 3/1957 | Terry et al. | 260/583 K |
| 2,856,428 | 10/1958 | Brown | 260/583 K X |
| 3,891,707 | 6/1975 | Waddan | 260/583 K |

FOREIGN PATENT DOCUMENTS

| | | | |
|---|---|---|---|
| 763109 | 8/1971 | Belgium | 564/492 |
| 521923 | 2/1956 | Canada | 564/493 |
| 40-13842 | 7/1965 | Japan | 564/493 |

OTHER PUBLICATIONS

Freidlin et al., "Chem. Ab.", Ab. No. 18578$^a$ (1961).
Polkovnikov et al., "Chem. Ab.", vol. 54, p. 1264 (1960).

*Primary Examiner*—John Doll
*Attorney, Agent, or Firm*—E. Eugene Innis; Russell L. Brewer

[57] ABSTRACT

This invention relates to a process for reducing amidine formation during reduction of organonitriles. The process comprises including a boron compound in the reaction medium in sufficient amount to complex the amidine compound as it is formed.

8 Claims, No Drawings

INHIBITING AMIDINE FORMATION DURING HYDROGENATION OF ORGANO NITRILES

BACKGROUND OF THE INVENTION

1. Field of the Invention

This invention relates to an improvement in a process for hydrogenating activated organonitriles to form the corresponding amines.

2. Description of the Prior Art

The hydrogenation of nitriles to form the corresponding amine is well-known in the prior art. Generally, the hydrogenation is carried out at temperatures of from 50° to 200° C., at pressures of from atmospheric to 3000 psig and in the presence of a hydrogenation catalyst, e.g. Raney nickel or other metal. Activated organonitriles, i.e. those in which the nitrile group has been activated by another group, generally an electron withdrawing group alpha or beta positioned to the nitrile group, have been difficult to reduce. One of the problems in the hydrogenation of these activated organonitriles is that hydrogenation results in the formation of compounds having an amidine linkage. Amidines not only are difficult to reduce to an amine structure, but their presence can influence the hydrogenation reaction and create problems downstream from the reaction, particularly in the separation.

Representative articles relating to the hydrogenation of nitriles include:

U.S. Pat. No. 3,369,002 discloses a process for producing compounds having amidine linkages therein and are produced in equilibrium by the reaction of a nitrile and ammonia.

U.S. Pat. No. 2,049,582 discloses a process for producing amidines by the reaction of a nitrile and an alkali amide. In the discussion of the prior art, the patentee noted that it was difficult to produce amidines in large quantities via the ammonolysis or ammonation of nitriles.

U.S. Pat. No. 2,252,723 discloses a process for producing halogen-alkyl amidines by reacting a haloamidoether with an amine or ammonia.

U.S. Pat. No. 3,733,325 discloses a process for producing aminoethylpiperizine by the catalytic hydrogenation of nitrilotriacetonitrile. Hydrogenation catalysts consisting of nickel or cobalt and optionally containing chromium and copper components are well suited for effecting hydrogenation at temperatures of 75°–200° C. and pressures of 1,000–3,000 psig.

U.S. Pat. No. 3,117,162 discloses a process for producing amines, e.g., propylamine, by the reduction of aliphatic nitriles, the reduction being in the presence of hydrogenation catalysts. Rhodium and platinum on carbon are suggested as hydrogenation catalysts with the hydrogenation being conducted in the liquid phase.

SUMMARY OF THE INVENTION

This invention relates to an improvement in a process for forming amines via the catalytic hydrogenation of an activated organo nitrile having from 2 to 16 carbon atoms, the nitrile being sufficiently active for forming by-product compounds having amidine linkages therein during the hydrogenation reaction. The improvement for reducing or inhibiting the formation of compounds having amidine linkages resides in complexing the compounds having the amidine linkages as they are formed with a boron compound during the hydrogenation reaction. In this regard, an effective proportion of a boron compound capable of complexing the amidine is added to the reaction medium prior to hydrogenation.

There are several advantages associated with this process, and these advantages include:

an ability to effect hydrogenation of various activated organonitriles, which normally result in the production of by-product compounds having amidine linkages therein, to produce amines in good yield; and an ability to reduce the formation of compounds having amidine linkages therein and thereby reduce problems in separating the amine product from by-product.

DESCRIPTION OF THE PREFERRED EMBODIMENT

Amidine formation can be a problem where an amine or ammonia is in contact with an activated nitrile, the amidine linkage being represented by the formula: HN=C—NH Compounds having the amidine linkage are extremely rare as a by-product in those processes where the nitrile is relatively inactive, e.g. propionitrile. On the other hand, as the nitrile group becomes activated, e.g. via the withdrawal of electrons from the nitrile group, the reactant nitrile can react with the product amine to produce the amidine linkage in substantial amounts. This can be shown by the reaction of methoxyethylamine and methoxyacetonitrile to yield an amidine of the formula:

$$CH_3OCH_2CN + CH_3OCH_2CH_2NH_2 \rightarrow CH_3OCH_2\overset{\overset{NH}{\|}}{C}-NHCH_2CH_2OCH_3$$

Activated organonitriles suited for the present process are those activated aliphatic or cyclic having from 3–16 carbon atoms in the structure. The nitriles typically are represented by the formula:

$$R-(X)-C-CN$$

where X is alpha or beta positioned to the nitrile group. Activation of the nitrile occurs by the presence of an electron withdrawing group on the alpha or beta carbon atom. X in the formula, for example, can represent an ether oxygen, an amine group, a nitro group, a nitrile group, a halogen atom, a sulfone group, a sulfamide group, a sulfur atom in the form of a sulfido group, a sulfoxide group, a O=C—O— group, an amide group, and a ketone carbonyl group $$(-\overset{\overset{O}{\|}}{C}-).$$

The remaining R can be virtually any carbon structure either linear or cyclic. specific examples of suited compounds include methoxyacetonitrile, methoxypropionitrile, iminodiacetonitrile, chloropropionitrile, aminoacetonitrile, N,N-dimethylaminoacetonitrile, nitrotriacetonitrile, bis(cyanomethyl)ether, and malonitrile.

Catalytic hydrogenation of the nitrile is carried out in conventional manner, e.g. utilizing temperatures of about 50°–200° C. and pressures from about atmospheric to 3,000 psig. Such conditions permit the reaction to be carried out in the vapor or liquid phase.

Often the hydrogenation of the nitrile to form the amine is carried out in the presence of a solvent preferably one that is inert to the reaction medium and one that does not poison the catalyst. Suitable solvents include benzene, acetic acid, butyl alcohol, hexand and the like and they may be present in various proportions, e.g. from about 1 to 99% by weight.

Hydrogenation catalysts used for the catalytic reduction of the activated organonitriles can be any of those used in the art. Generally, these are metals, particularly the Group 6 or Group 8 metals and these catalysts generally include rhodium, palladium, ruthenium, nickel, cobalt, platinum, chromium and copper as a component. The metals generally are present upon a support such as carbon, alumina, alumina-silica, silica, kieselguhr, calcium carbonate, barium sulfate, bentonite, and the like. The active metal generally is present in a proportion of from about 0.1 to 60% by weight, and generally 1 to 20%.

The key to the invention is the complexing of the compound having amidine linkages therein early in the catalytic hydrogenation or reduction of the activated nitrile compound. Amidines are self-catalyzing and once formed tend to catalyze their formation, the amidine being formed by the reaction between the activated nitrile and amine product. By complexing the inital quantities of compound having amidine linkage therein, the effect of the amidine in self-catalyzing its own formation is minimized and therefore the presence of by-products having the amidine linkage is greatly reduced. In other words, by complexing a sufficient amount of the initial quanitity of amidine formed, the reduction of the nitrile to the amine can proceed rapidly with little by-product formation.

Complexing of the by-product having the amidine linkage therein is accomplished via the incorporation of boron compound into the reduction reaction. Examples of boron compounds include boron salts of carboxylic acids having from 1-10 carbon atoms, e.g. boron acetate, boron propionate, boron butyrate; boron phosphates, e.g. boron triphosphate; alkyl borates, preferably $C_{1-3}$ alkyl borates, e.g. tri-n-propyl borate, trimethyl borate, triethyl borate; boric acid and salts of these acids, e.g. boron oxide, boron halide, e.g. boron trifluoride and boron trifluoride and amino boron compounds, e.g. triethanolamine borate.

The boron compound is included in the reduction reaction in an amount to provide at least an effective proportion of boron atom to complex the initial by-products containing the amidine linkages. An effective proportion is that portion where the amount of by-product containing amidine linkage is reduced as compared to a system where no complexing agent is used. Surprisingly then, a stoichiometric quantity of complexing agent based on orgnano nitrile or amidine capable of being formed is not required in the process. Because the rate of reduction of the nitrile to the amine is relatively rapid, and the initial catalytic quantities of amidine are complexed, there is insufficient time for the compounds having amidine linkages to be formed in substantial quantities. Typically, the boron proportions used for complexing the by-products containing amidine linkages are provided at levels from about 0.0005 to 1 gram atom boron per gram mole of activated nitrile reactant. Preferred ranges are from about 0.01 to 0.5 g atoms/g mole. Quantities of boron compound which provide more than about 1 weight part boron atom per mole nitrile do not provide significant advantages, at least in terms of inhibiting the formation of compounds having the amidine linkage therein. On the other hand, as the quantity of complexing agent is reduced, particularly toward the low end of the range specified, larger proportions of compounds having amidine linkages may be produced.

If a liquid phase reduction of the activated organonitrile is used, and generally this is preferred the complexing agent should be dispersible in the liquid phase. In general, the organoboron compounds should be soluble in the reaction medium or the carrier solvent in which the reaction is carried out. Complexing of the amidine using a complexing agent which is homogeneous with the reaction medium reduced the formation of by-product amidine.

The following examples are provided to illustrate preferred embodiments of the invention and are not intended to restrict the scope thereof.

EXAMPLE 1

Several runs were made to determine the stability of methoxyacetonitrile (MACN) with methoxyethylamine (MENH$_2$) with various boron and phosphorous complexing agents. In each run, the MACN and MENH$_2$ were first dissolved 50 ml methanol and divided into 10 ml aliquots. The complexing agent, at various weight levels, then was added to a 10 ml aliquot of the MACN-MENH$_2$ methanol solution. A control (untreated sample) was also formed. The samples were analyzed periodically in both the untreated and treated samples for amidine formation. Decomposition times longer than the untreated control indicate an ability to inhibit amidine formation during the reduction of the nitrile. In Table I, (mm) refers to millimoles and the decomposition time is expressed in hours, mole % refers to the moles complexing agent divided by the moles nitrile and is expressed in percent. The addition of complexing agent to the reaction was varied from 0.1 to 1 gram.

TABLE 1

| Run | MACN (mm) | MENH$_2$(mm) | Complexing Agent | Level (Agent) g | Mole Percent | Decomposition Time Untreated (hr.) | Treated Time Decomposition (hr.) |
|---|---|---|---|---|---|---|---|
| 1 | 36.8 | 74.9 | ortho boric acid | 0.1 | 24 | 10.5 | 40 |
| 2 | " | " | " | 1 | 240 | 10.5 | 40 |
| 3 | " | " | boron acetate | 0.1 | 7.5 | 10.5 | 39 |
| 4 | " | " | " | 1 | 75 | 10.5 | 39 |
| 5 | " | " | tri-n-propyl borate | 0.1 | 7.5 | 10.5 | 74 |
| 6 | " | " | " | 1.0 | 75 | 10.5 | 74 |
| 7 | 36.8 | 374.5 | trimethyl borate | 0.1 | 14.4 | 43 | 191.5 |
| 8 | " | " | " | 1.0 | 144 | 43 | 191.5 |
| 9 | " | " | tri-n-propyl borate | 0.1 | 7.5 | 43 | 200 |
| 10 | " | " | " | 1.0 | 75 | 43 | 200 |
| 11 | 36.8 | 74.9 | orthophosphoric acid | 0.1 | 18 | 10.5 | 10.4 |
| 12 | " | " | " | 1.0 | 180 | 10.5 | 1.0 |
| 13 | " | " | potassium dihydrogen | 0.1 | 180 | 10.5 | 10.5 |

TABLE 1-continued

| Run | MACN (mm) | MENH₂(mm) | Complexing Agent | Level (Agent) g | Mole Percent | Decomposition Time Untreated (hr.) | Treated Time Decomposition (hr.) |
|---|---|---|---|---|---|---|---|
| 14 | " | " | phosphate potassium dihydrogen phosphate | 1.0 | 110 | 10.5 | 5.0 |
| 15 | " | " | dipotassium hydrogen phosphate | 0.1 | 5.9 | 10.5 | 5.0 |
| 16 | " | " | dipotassium hydrogen phosphate | 1.0 | 5.9 | 10.5 | 5.0 |

The results for Table 1 show that all of the boron compounds were effective in inhibiting amidine formation while the phosphorous compounds were not effective. Ortho phosphoric acid, in fact, catalyzed the formation of amidine. The alkyl borates provided the best results and this may have been due to the greater solubility of that compound as compared to the inorganic complexes in the reaction medium.

EXAMPLE 2

The procedure of Example 1 was repeated except that methoxypropionitrile (MPN) and methoxypropylamine (MPNH₂) were substituted for the methoxyethylamine. All other procedures remained the same.

As the results in Table 2 show, the boron compounds tended to stabilize the mixture of amine and nitrile.

EXAMPLE 3

The procedure of Example 1 was repeated except that a iminodiacetonitrile (IDA) and ethylene diamine (EDA), diethylene triamine (DETA) and monoethylamine (MEA) were substituted for the nitrile and amine respectively. Various boron compounds then were tested to determine their effectiveness in preventing amidine formation between the iminodiacetonitrile and ethylene diamine.

Table 3 shows that the boron compounds are effective in extending the decomposition time for each situation. Better results are noted at the 1 gram weight level or about the 0.05 gram atom level of boron.

TABLE 2

| Run | MPN (mm) | MPNH₂(mm) | Complexing Agent | Level (Agent) g | Mole Percent | Decomposition Time Untreated (hr.) | Treated Time Decomposition (hr.) |
|---|---|---|---|---|---|---|---|
| 1 | 36.8 | 74.9 | tri-n-propyl borate | 0.1 | 7.5 | 208 | 700 |
| 2 | " | " | " | 1.0 | 75 | 208 | 700 |
| 3 | " | " | boron acetate | 0.1 | 7.5 | 208 | 700 |
| 4 | " | " | " | 1.0 | 75 | 208 | 700 |

TABLE 3

| Run | IDAN (mm) | Amine (mm) | Complexing Agent | Level (Agent) g | Mole Percent | Decomposition Time Untreated (hr.) | Treated Time Decomposition (hr.) |
|---|---|---|---|---|---|---|---|
| 1 | 36.8 | EDA 74.9 | boron phosphate | 0.1 | 13.0 | 3.6 | 31.0 |
| 2 | " | " | boric acid | 0.1 | 24 | 3.6 | 7.5 |
| 3 | " | " | boric acid | 1.0 | 240 | 3.6 | 12.0 |
| 4 | " | " | phenyl boric acid | 0.1 | 12 | 3.6 | 8.9 |
| 5 | " | " | boron acetate | 0.1 | 7.5 | 3.6 | 26.0 |
| 6 | " | " | tri-n-propyl borate | 0.1 | 7.5 | 3.6 | 22.5 |
| 7 | " | " | tri(methoxyethyl) borate | 0.1 | 7.5 | 4.0 | 7.5 |
| 8 | " | EDA 374.6 | boron acetate | 0.1 | 7.5 | 4.0 | 10.0 |
| 9 | " | " | tri-n-propyl borate | 0.1 | 7.5 | 4.0 | 5.5 |
| 10 | " | EDA 74.9 | boron oxide | 0.1 | 21.0 | 3.6 | 7.5 |
| 11 | " | EDA 74.9 | boron oxide | 1.0 | 210 | 3.6 | 12.8 |
| 12 | " | " | triethanolamine borate | 0.1 | 9.5 | 3.6 | 17.0 |
| 13 | " | " | triethanolamine borate | 1.0 | 95 | 3.6 | 17.0 |
| 14 | " | " | 1:1 boric acid EDA adduct | 0.1 | 4.0 | 3.6 | 9.0 |
| 15 | " | " | 1:1 boric acid EDA adduct | 1.0 | 40 | 3.6 | 9.0 |
| 16 | " | " | trimethyl borate | 0.1 | 14.4 | 3.6 | 18.0 |
| 17 | " | " | " | 1.0 | 144 | 3.6 | 18.0 |
| 18 | " | DETA 374.6 | tri-n-propyl borate | 0.1 | 7.5 | 11.0 | 20.0 |
| 19 | " | " | " | 1.0 | 75 | 11.0 | 40 |
| 20 | " | " | trimethyl borate | 0.1 | 14.4 | 11.0 | 29.5 |
| 21 | " | " | " | 1.0 | 144 | 11.0 | 29.5 |
| 22 | " | MEA 374.6 | tri-n-propyl borate | 0.1 | 7.5 | 1.6 | 13.6 |
| 23 | " | " | boron acetate | 0.1 | 7.5 | 1.6 | 13.6 |

EXAMPLE 4

The procedure of Example 3 using IDAN and EDA was repeated except that Raney Nickel and Raney Cobalt were included in the reaction medium and run as a control. The amounts of Raney Nickel at the 0.6 and 0.06 g levels in the reaction medium approximated the conditions that would be encountered in conventional reactions for the reduction of the nitrile.

As is shown in Table 4, the presence of Raney Nickel and Raney Cobalt catalyzes the formation of amidines as the decomposition time is much lower than in the untreated state. When tri-n-propyl borate was included in the reaction medium, the decomposition time was greatly extended thus retarding the catalytic effect on the reaction of the IDAN and EDA to form amidines.

TABLE 4

| Run | MPN (mm) | MPNH$_2$(mm) | Complexing Agent | Level (Agent) g | Mole Percent | Decomposition Time Untreated (hr.) | Treated Time Decomposition (hr.) |
|---|---|---|---|---|---|---|---|
| 1 | 36.8 | 74.9 | Raney Nickel | 0.6 | 100 | 3.6 | 0.2 |
| 2 | " | " | Raney Cobalt | 0.6 | 100 | 3.6 | 0.2 |
| 3 | " | " | Raney Nickel/ Tri-n-propyl borate | 0.6/0.1 | 15.25/7.9 | 3.6 | 8.2 |
| 4 | " | " | Raney Cobalt/ Tri-n-propyl borate | 0.06/0.1 | 15.25/7.9 | 3.6 | 35.0 |

What is claimed is:

1. In a process for forming amines and a by-product compound having amidine linkages therein by the catalytic hydrogenation of an activated organonitrile having from 2–16 carbon atoms in the structure, the improvement for inhibiting the formation of such compounds having amidine linkages therein which comprises including a boron compound in the hydrogenation reaction in sufficient proportion for complexing the compounds having amidine linkages therein as they are formed with boron compound.

2. The process of claim 1 wherein said activated organonitrile is activated by an electron withdrawing group.

3. The process of claim 2 wherein said activated electron withdrawing group is selected from the group consisting of a halogen, an alkoxy, a sulphone, an amino, an imino, a

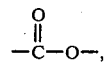

an ether oxygen, carbonyl, a sulfide and a sulfamide group.

4. The process of claim 3 wherein said activated organonitrile is an alicyclic nitrile having from 2 to 8 carbon atoms in the structure.

5. The process of claim 3 or 4 wherein said boron compound is selected from the group consisting of a $C_{1-3}$ alkyl borate, a boron salt of a carboxylic acid, said acid having from 1 to 10 carbon atoms, boric acid and salts, boron halide, amino boron compounds and boron phosphate.

6. The process of claim 5 wherein said organonitrile is selected from the group consisting of iminodiacetonitrile, bis(cyanoalkyl) ether where the alkyl group has 1 or 2 carbon atoms, methoxy acetonitrile, methoxy propionitrile and nitrotriacetonitrile.

7. The process of claim 3, wherein said boron compound is present in a proportion to provide from about 0.0005 to 1 gram atoms boron per gram mole of nitrile.

8. The process of claim 6 wherein said boron compound is present in a proportion to provide from 0.01 to 0.5 gram atoms boron per gram mole of nitrile.

* * * * *

UNITED STATES PATENT AND TRADEMARK OFFICE
CERTIFICATE OF CORRECTION

PATENT NO. : 4,313,005

DATED : 26 January 1982

INVENTOR(S) : Michael E. Ford et al

It is certified that error appears in the above-identified patent and that said Letters Patent are hereby corrected as shown below:

Column 2, Line 58
  Delete "specific" and substitute therefor
  --Specific--.

Column 3, Line 5
  Delete "hexand" and substitute therefor --hexane--.

Column 2, lines 61-62 Delete "nitrotriacetonitrile" and substitute therefor -- nitrilotriacetonitrile --
Column 8, Claim 6, Line 37
  Delete "nitrotriacetonitrile" and substitute
  therefore --nitrilotriacetonitrile--.

Signed and Sealed this

Seventh Day of December 1982

[SEAL]

Attest:

GERALD J. MOSSINGHOFF

Attesting Officer   Commissioner of Patents and Trademarks